US007103140B2

(12) United States Patent
Amitani et al.

(10) Patent No.: US 7,103,140 B2
(45) Date of Patent: *Sep. 5, 2006

(54) RADIATION IMAGE RADIOGRAPHIC APPARATUS

(75) Inventors: Kouji Amitani, Hachioji (JP); Takahiro Mitsumoto, Hachioji (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 10/719,332

(22) Filed: Nov. 20, 2003

(65) Prior Publication Data

US 2004/0109530 A1 Jun. 10, 2004

(30) Foreign Application Priority Data

| Nov. 26, 2002 | (JP) | 2002-343117 |
| Dec. 26, 2002 | (JP) | 2002-377723 |
| Sep. 5, 2003 | (JP) | 2003-313620 |

(51) Int. Cl.
*A61B 6/04* (2006.01)
*G01N 23/04* (2006.01)
*G03B 42/02* (2006.01)

(52) U.S. Cl. .................. 378/37; 378/53; 378/62; 378/174; 378/189

(58) Field of Classification Search .................. 378/37, 378/91, 115, 116, 167–170, 174, 177–182, 378/189, 196, 197, 51, 53–55, 62; 600/407, 600/425
See application file for complete search history.

(56) References Cited

U.S. PATENT DOCUMENTS

| 2,680,199 | A | * | 6/1954 | Abel .......................... 378/27 |
| 4,251,732 | A | * | 2/1981 | Fried ......................... 378/170 |
| 4,394,737 | A | * | 7/1983 | Komaki et al. ............... 378/23 |
| 4,599,738 | A | * | 7/1986 | Panetta et al. ................ 378/37 |
| 4,855,598 | A | * | 8/1989 | Ohgoda et al. ............. 250/582 |
| 5,018,176 | A | * | 5/1991 | Romeas et al. ............... 378/37 |
| 5,022,065 | A | * | 6/1991 | Wijkstrom ................. 378/168 |
| 5,177,778 | A | * | 1/1993 | Tsurumaki et al. ......... 378/117 |
| 5,473,664 | A | * | 12/1995 | Strawder .................... 378/177 |
| 5,737,386 | A | * | 4/1998 | Strawder ..................... 378/95 |
| 5,917,877 | A | * | 6/1999 | Chiabrera et al. .......... 378/207 |
| 6,226,353 | B1 | * | 5/2001 | Wilkins et al. ............ 378/98.9 |
| 6,273,606 | B1 | * | 8/2001 | Dewaele et al. ............ 378/174 |
| 6,744,062 | B1 | * | 6/2004 | Brahm et al. ............... 378/174 |
| 6,934,361 | B1 | * | 8/2005 | Ohkoda ..................... 378/98.8 |
| 6,934,409 | B1 | * | 8/2005 | Ohara ........................ 382/132 |
| 7,027,556 | B1 | * | 4/2006 | Ohara .......................... 378/62 |

FOREIGN PATENT DOCUMENTS

JP          2001-238871 A     9/2001

* cited by examiner

*Primary Examiner*—Allen C. Ho
(74) *Attorney, Agent, or Firm*—Frishauf, Holtz, Goodman & Chick, P.C.

(57) ABSTRACT

A user-friendly, inexpensive radiation image radiographing apparatus capable of easily switching between absorption contrast image radiography and phase contrast image radiography. The radiation image radiographing apparatus has: a radiation source; a subject platform for supporting a subject so as to face the subject to the radiation source; and a plurality of supporting platforms for supporting a radiation image information detecting member at a side opposite to the radiation source with respect to the subject platform, the radiation image information detecting member for detecting radiation image information based on radiation transmitted through the subject, wherein distances between the plurality of supporting platforms and the radiation source are different from each other.

19 Claims, 7 Drawing Sheets

RADIATION IMAGE RADIOGRAPHIC APPARATUS

BACKGROUND OF THE INVENTION

1. Field of the Invention

The present invention relates to a radiation image radiographing apparatus, in particular, a radiation image radiographing apparatus capable of radiographing a phase contrast image.

2. Related Art

Generally, a radiation image radiographing apparatus using a mechanism of transmitting radiation through a substance is widely used for a medical image diagnosis, a non-destructive inspection and the like. In particular, in a radiation image radiographing apparatus for mammography, which is used for radiographing a specific region of body, radiography of a subject fixed on a subject platform which is combined with a radiation image information detecting member has been performed. However, since the subject is radiographed at substantially full scale with this method, contrast of the radiographed image is insufficient. Thereby, the radiation image radiographing apparatus is not capable of radiographing an image clear enough to provide fine structure of the specific region of a body for interpretation.

Accordingly, a method of obtaining a phase contrast image by use of a radiation tube (a small focus radiation source having a focus size within the range from 30 μm to 300 μm), which is used in general medical institutions, is known (for example, refer to Japanese Patent Application Publication (Unexamined) No. Tokukai 2001-238871). With this method, it is possible to render a border with higher contrast, and thereby obtain a clearer and finer image than the normal absorption contrast image. However, in order to obtain such a phase contrast image, it is necessary to have predetermined distance between the subject and the radiation image information detecting member. Further, in view of reducing a subject's burden and considering cost to spend on equipment in a medical scene, ideally, the radiographing apparatus should be capable of performing radiography in both "phase contrast image radiography mode" for radiographing a phase contrast image and "absorption contrast image radiography mode" for radiographing only an absorption contrast image.

Accordingly, in an earlier art, a structure where a supporting member for supporting the radiation image information detecting member is placed and capable of moving vertically along a rail, and thereby it is possible to change the distance between the subject and the radiation image information detecting member, is used. Therefore, in the earlier art, the radiographing apparatus is capable of radiographing both a normal absorption contrast image and a phase contrast image.

However, with the method in the earlier art, since the supporting platform is capable of moving its location arbitrarily, a magnifying rate of the image also changes countlessly. Therefore, it is necessary for an operator to adjust the magnifying rate for radiographing. Consequently, when it is necessary to obtain images with the same magnifying rate, even though calibration of the magnifying rate is provided, it is not easy to make a fine adjustment.

Further, since it is also necessary to have a location recognition device as a means to recognize a location for obtaining information of distance between a radiation source and the subject platform (with which the subject is in contact) and the distance between the subject platform and the radiation image information detecting member, control radiation dose based on the information and the like, the control becomes more complicated.

Furthermore, since it is necessary to have such a complicated control means as mentioned above, it causes an increase on cost of the apparatus.

SUMMARY OF THE INVENTION

The present invention is to solve the above-mentioned problems.

An object of the present invention is to provide a user-friendly, inexpensive radiation image radiographing apparatus capable of easily radiographing both an absorption contrast image and a sharp phase contrast image without a location adjustment of a supporting platform nor a fine adjustment on a magnifying rate.

In accordance with a first aspect of the present invention, a radiation image radiographing apparatus comprises: a radiation source; a subject platform for supporting a subject so as to face the subject to the radiation source; and a plurality of supporting platforms for supporting a radiation image information detecting member in a side opposite to the radiation source with respect to the subject platform, the radiation image information detecting member detecting radiation image information based on radiation transmitted through the subject, wherein a distance between one supporting platform and the radiation source is different from a distance between one of the other supporting platforms and the radiation source.

According to the radiation image radiographing apparatus of the first aspect of the present invention, since the radiation image radiographing apparatus comprises a plurality of radiation image information detecting members, an operator only needs to choose any one among the plurality of radiation image information detecting members for performing radiography. Therefore, the operator does not have to make a fine adjustment on a magnifying rate or the like, and it is possible to easily repeat the radiography of a predetermined magnifying rate. In other words, in both the cases of radiographing a normal absorption contrast image and radiographing a phase contrast image, since the operator only needs to choose any one of the plurality of radiation image information detecting members attached to each of the plurality of supporting platforms for switching a radiography mode, it is possible to easily switch a radiography mode. Further, since it is also possible to switch a mode of magnifying radiography by attaching a radiation image information detecting member to a predetermined supporting platform or the like, it is possible to simplify a structure of the apparatus, and thereby it is possible to improve user-friendliness and reduce cost on the apparatus.

Preferably, in the apparatus of the first aspect of the present invention, at least one of the plurality of supporting platforms is placed where radiographing an absorption contrast image can be performed, and the other plurality of supporting platforms than the at least one of the plurality of the supporting platforms are placed where radiographing a phase contrast image can be performed.

According to the apparatus, an apparatus is capable of radiographing in both an absorption contrast image radiography mode and a phase contrast image radiography mode.

Preferably, in the apparatus of the first aspect of the present invention, the plurality of supporting platforms are placed so as to fix distances from the radiation source thereto.

According to the apparatus, since the distances between the plurality of supporting platforms and the radiation source are fixed, the operator is able to uniformly obtain predetermined magnifying rates and thereby user-friendliness of the apparatus improves.

Preferably, the apparatus of the first aspect of the present invention, further comprises a controller having a switcher for switching a radiography mode corresponding to each of the plurality of supporting platforms, wherein the controller controls irradiation conditions of the radiation source according to information from the switcher.

According to the apparatus, since an optimal irradiation condition of the radiation source is determined without the operator making a special operation except for switching a radiography mode, it is possible to radiograph both an absorption contrast image and a phase contrast image, and thereby the user-friendliness of the apparatus improves.

More preferably, each of the plurality of supporting platforms comprises a sensor for detecting whether the each of the plurality of supporting platforms comprising the sensor is usable for radiography, and the controller automatically obtains the radiography mode in the case of performing phase contrast image radiography when the sensor recognizes a status of each of the plurality of supporting platforms.

According to the apparatus, when a phase contrast image is radiographed, it is possible to automatically determine a radiography mode without the operator making a special operation, and thereby the user-friendliness of the apparatus further improves.

More preferably, when a magnified image is radiographed in the radiography mode of phase contrast image radiography, the controller reduces a size of the magnified image back to substantially full scale to be output.

According to the apparatus, it is possible to use both a magnified image and an image reduced back to substantially full scale from the magnified image.

Preferably, in the apparatus of the first aspect of the present invention, the radiation image information detecting member is a photostimulable phosphor plate.

According to the apparatus, by using the photostimulable phosphor plate as the radiation image information detecting member, it is possible to record radiation image information of the subject in the photostimulable phosphor plate by use of a property of accumulative phosphor (stimulable phosphor) emitting light according to radiation energy irradiated to the subject, for providing an image of the subject.

Preferably, in the apparatus of the first aspect of the present invention, the radiation image information detecting member is a flat panel detector.

According to the apparatus, by using the flat panel detector as the radiation image information detecting member, it is possible to record radiation image information of the subject by detecting intensity of the radiation irradiated to the subject, for providing an image of the subject.

Preferably, the apparatus of the first aspect of the present invention further comprises an input device for inputting a radiography mode.

More preferably, the input device is a radiation operation panel composed of keys capable of selecting the radiography mode.

According to the apparatus, when a phase contrast image is radiographed, it is possible to choose any radiography mode of magnifying rates easily. Further, it is possible to easily choose a magnifying rate by inputting it at the radiation operation panel.

Preferably, in the apparatus of the first aspect of the present invention, at least one of the plurality of supporting platforms is capable of being evacuated from a location where the at least one of the plurality of supporting platforms faces the radiation source.

More preferably, when the at least one of the plurality of supporting platforms is evacuated from the location where the at least one of the plurality of supporting platforms faces the radiation source, space opposite to the radiation source with respect to the subject platform is secured.

According to the apparatus, since at least one of the plurality of supporting platforms is capable of being evacuated from the location where the at least one of the plurality of supporting platforms faces the radiation source so as to secure the space opposite to the radiation source with respect to the subject platform, when the supporting platform capable of being evacuated is not used for radiography, it is possible to prevent from the supporting platform capable of being evacuated interfering an examinee by evacuating the supporting platform capable of being evacuated. As a result, it is possible to reduce a burden on the examinee.

Further, as long as the supporting platform capable of being evacuated is evacuated from an irradiation field of the radiation source, although the supporting platform capable of being evacuated is still supporting the radiation image information detecting member, the radiation source does not irradiate radiation to the radiation image information detecting member. Therefore, for example, in the case of using a radiation image information detecting member having silver halide photographic film, it is possible to prevent from wasting the silver halide photographic film.

Preferably, in the apparatus of the first aspect of the present invention, at least one of the plurality of supporting platforms detachably supports the radiation image information detecting member.

According to the apparatus, since at least one of the plurality of supporting platforms detachably supports the radiation image information detecting member, when one of the other plurality of supporting platforms is used for radiography, it is only necessary to detach the radiation image information detecting member from the detachable supporting platform. As a result, even if the detachable supporting platform is not evacuated from the irradiation field of the radiation source, for example, in the case using a radiation image information detecting member having silver halide photographic film, it is possible to prevent from wasting the silver halide photographic film.

Preferably, in the apparatus of the first aspect of the present invention, at least one of the plurality of supporting platforms is capable of being attached to and being detached from a body of the radiation image radiographing apparatus.

According to the apparatus, in the case of not using the supporting platform capable of being attached to and being detached from a body of the radiation image radiographing apparatus, as long as the supporting platform capable of being attached to and being detached from is detached from the body of the radiation image radiographing apparatus, it is possible to prevent from the supporting platform capable of being attached to and being detached from interfering the examinee, and thereby reduce a burden on the examinee.

Preferably, in the apparatus of the first aspect of the present invention, at least one of the plurality of supporting platforms is capable of lying and standing.

According to the apparatus, since at least one of the plurality of supporting platforms is capable of lying and standing, it is possible to move the supporting platform capable of lying and standing to a location where it does not interfere the examinee without detaching it. In other words, without detaching it, it is possible to evacuate the supporting platform capable of lying and standing to the location where it does not interfere the examinee, and thereby reduce a burden on the examinee. Further, since it is not necessary to detach the supporting platform capable of lying and standing, it is not necessary to reserve space for the supporting platform capable of lying and standing.

Preferably, in the apparatus of the first aspect of the present invention, at least one of the plurality of supporting platforms is capable of extending and shrinking.

According to the apparatus, since at least one of the plurality of supporting platforms is capable of extending and shrinking, it is possible to perform radiography with the radiation image information detecting member put on the stretched supporting platform capable of stretching and shrinking within the irradiation field of the radiation source, and also it is possible to prevent from the supporting platform capable of extending and shrinking interfering the examinee by shrinking the supporting platform capable of extending and shrinking. Consequently, since it is not necessary to detach the supporting platform capable of extending and shrinking, it is not necessary to reserve space for the supporting platform capable of extending and shrinking.

Preferably, in the apparatus of the first aspect of the present invention, at least one of the plurality of supporting platforms is capable of moving along an irradiation direction of the radiation from the radiation source.

According to the apparatus, since at least one of the plurality of supporting platforms is capable of moving along an irradiation direction of the radiation from the radiation source, when the supporting platform capable of moving is in contact with the subject platform, the radiation image information detecting member supported by the supporting platform capable of moving is capable of detecting radiation not only when a phase contrast image is radiographed but also when an absorption contrast image is radiographed.

Further, when the supporting platform capable of moving is not used for radiography, by evacuating the supporting platform capable of moving, it is possible to prevent from the supporting platform capable of moving interfering the examinee.

Preferably, in the apparatus of the first aspect of the present invention, at least one of the plurality of supporting platforms is capable of rotating from a location where the at least one of the plurality of supporting platforms faces the radiation source toward a side of the radiation source or a side opposite to the radiation source.

More preferably, the at least one of the plurality of supporting platforms comprises a cut portion, and when the at least one of the plurality of supporting platforms rotates, at least a part of one of the other plurality of supporting platforms and the subject platform passes through the cut portion.

According to the apparatus, since at least one of the plurality of supporting platforms is capable of rotating from a location where the at least one of the plurality of supporting platforms faces the radiation source toward one of a side of the radiation source and a side opposite to the radiation source, and comprises a cut portion and when the supporting platform capable of rotating rotates, at least a part of one of the other plurality of supporting platforms and the subject platform pass through the cut portion, the supporting platform comprising the cut portion is able to rotate without any interference from the other supporting platforms and the subject platform. Accordingly, since it is possible to evacuate the supporting platform comprising the cut portion from the space opposite to the radiation source with respect to the subject platform, it is possible to easily evacuate unused supporting platforms with operator's operationality kept with an easier structure than the cases of moving the supporting platform capable of moving along the irradiation direction, extending and shrinking the supporting platform capable of extending and shrinking, attaching and detaching the supporting platform capable of being attached to and being detached from and folding the supporting platform capable of folding.

More preferably, at least two of the plurality of supporting platforms are supporting platforms for phase contrast image radiography.

According to the apparatus, since at least two of the plurality of supporting platforms are located in the space opposite to the radiation source with respect to the subject platform and therefore they could interfere radiography, by evacuating the at least two supporting platforms from the space, it is possible to easily perform radiography.

More preferably, sizes of the plurality of supporting platforms and the subject platform decrease as distances thereof from the radiation source become shorter.

According to the apparatus, since sizes of the plurality of supporting platforms and the subject platform decrease as distances thereof from the radiation source become shorter, when one supporting platform rotates from the location where facing the radiation source toward the side of radiation source, the other supporting platforms and the subject platform are able to pass through the cut portion of the one supporting platform.

More preferably, the radiation image information detecting member supported by a supporting platform located the closest to the radiation source among the plurality of supporting platforms is larger than the subject.

According to the apparatus, since a supporting platform located the closest to the radiation source among the plurality of supporting platforms is larger than the subject, it is possible to surely detect radiation image information based on radiation transmitted through the subject on the radiation image information detecting member. In other words, it is possible to surely radiograph a radiation image of the subject.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein.

AN EMBODIMENT OF THE INVENTION

First Embodiment

Hereinafter, an embodiment of the invention will be explained. However, the invention is not limited to the embodiment explained hereafter. Further, there are descriptions where meanings of words are explained hereinafter, but the descriptions are only to explain the meanings of the words, and the meanings of the words are not limited to the descriptions.

Figure 1:
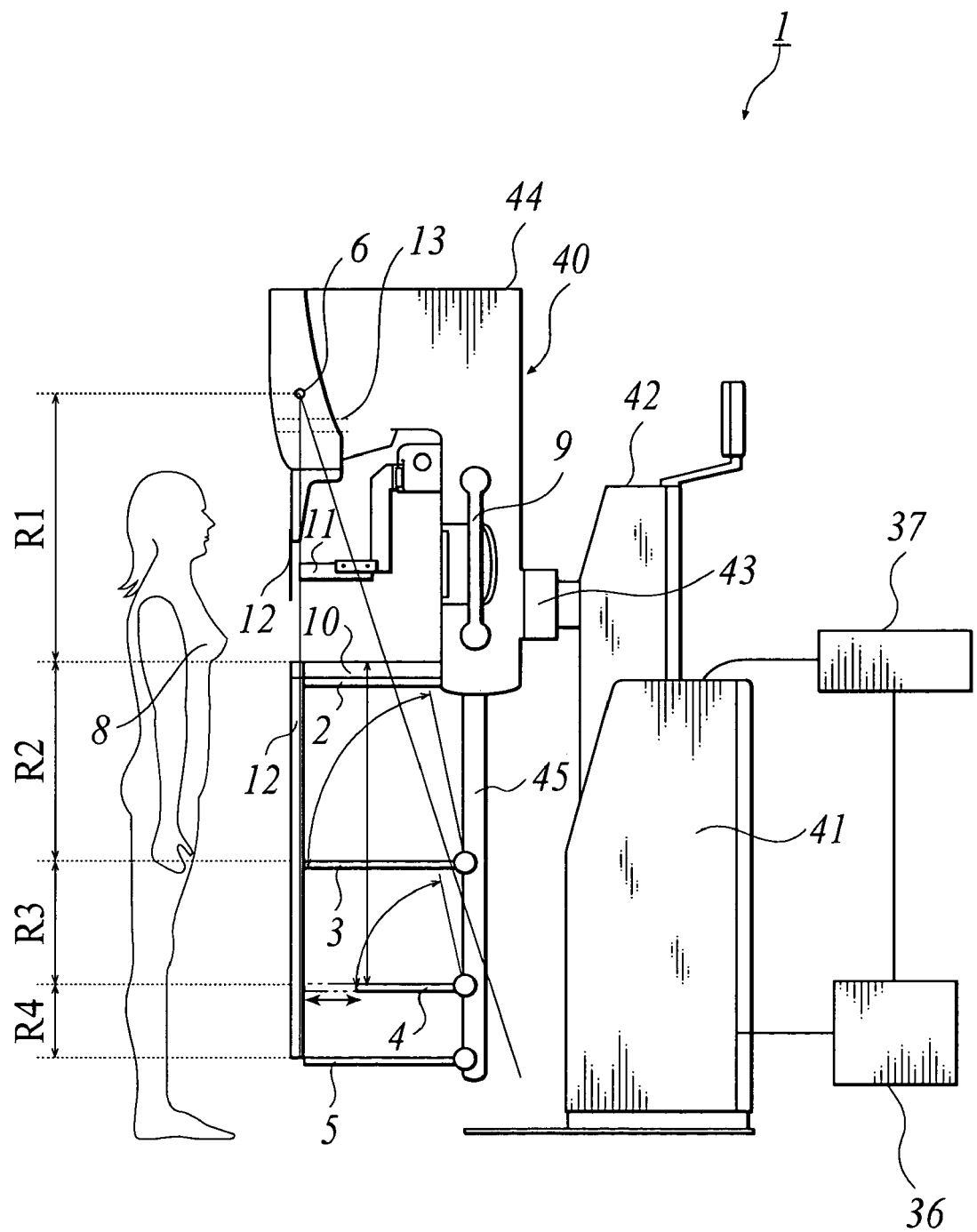
FIG. 1 is a side view showing a radiation image radiographing apparatus 1 in a first embodiment applied to the present invention.
Figure 2:
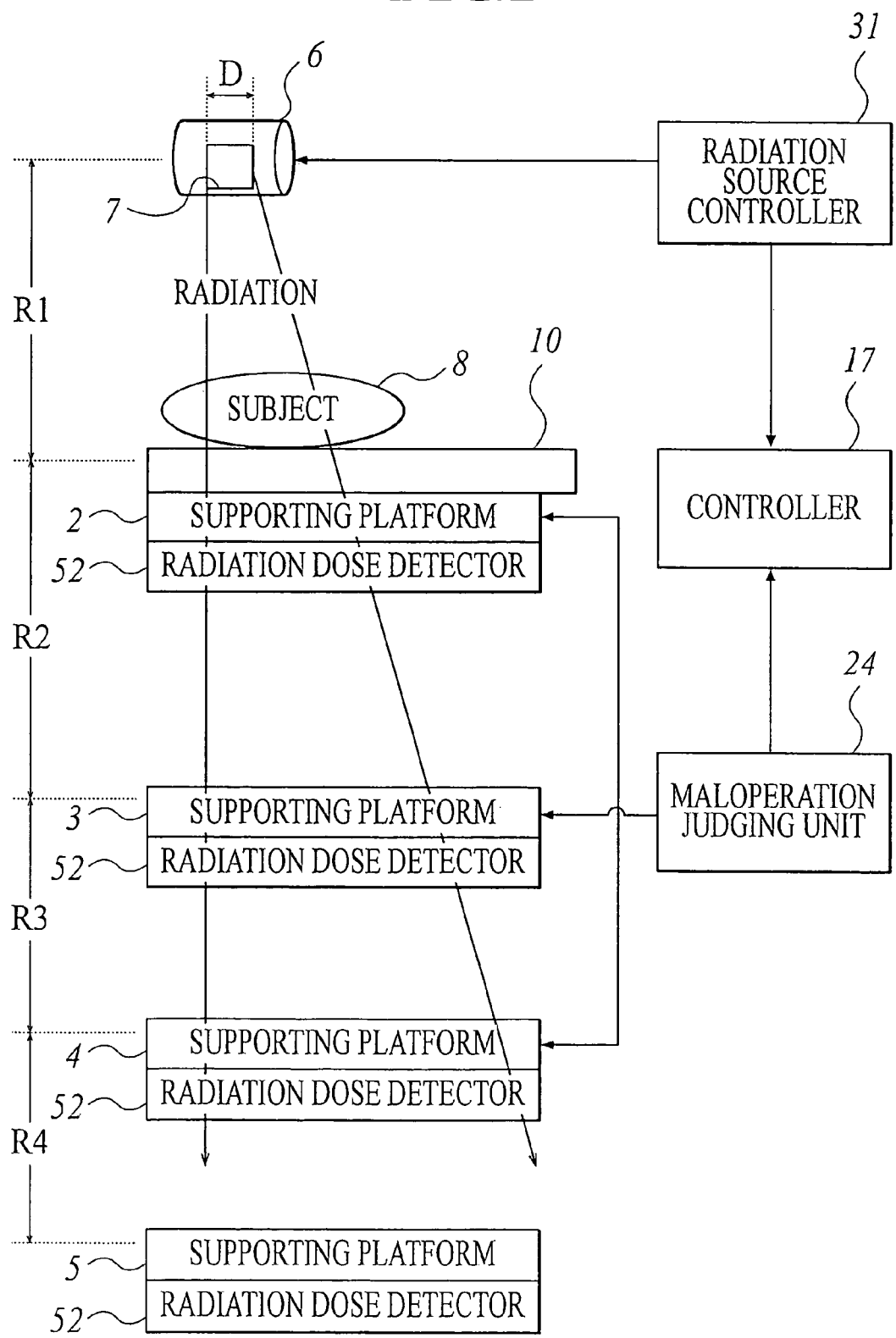
FIG. 2 is a pattern diagram showing a whole structure of the radiation image radiographing apparatus 1.

FIG. 1 is a side view showing a radiation image radiographing apparatus 1 in a first embodiment applied to the present invention. FIG. 2 is a pattern diagram showing a whole structure of the radiation image radiographing apparatus 1.

As shown in FIG. 1, the radiation image radiographing apparatus 1 comprises an apparatus body 40, a controller 17 (shown in FIG. 4), a radiation operation panel 37 having keys for selecting a radiography mode, a power supply 36 as a power source of the whole radiation image radiographing apparatus 1, supporting platforms 2, 3, 4 and 5 for supporting radiation image information detecting members capable of detecting radiation image information based on radiation transmitted through a subject, and a supporting portion 45 for supporting the supporting platforms 2, 3, 4 and 5.

The apparatus body 40 comprises a first supporting base 41 standing at an installation site, a second supporting base 42 capable of moving vertically along the first supporting base 41, a spindle 43 placed in front of the second supporting base 42, and a radiography unit 44 supported by the spindle 43 as capable of rotating around the spindle 43.

The radiation operation panel 37 and the power supply 36 are connected to the first supporting base 41.

At the upper part of the radiography unit 44, a radiation source 6 is placed. The power supply 36 is connected to the radiation source 6, and impresses tube voltage to the radiation source 6. At an irradiation gate of the radiation source 6, a window of an aperture 13 for adjusting an irradiation field is placed as capable of opening and shutting. As the radiation source 6, an X-ray tube used in a general medical institution and having a focus within a range from 30 to 3000 µm, preferably from 30 to 1000 µm, is used. In detail, a radiation tube irradiating radiation with wavelength from 0.01 nm to 0.1 nm is used as the radiation source 6. Radiation is irradiated by converting kinetic energy into radiation energy in the radiation tube, the kinetic energy obtained by accelerating electrons generated by thermal excitation with high voltage and crashing them into an anode. When a radiation image is radiographed, the accelerating voltage is set as tube voltage, the number of the generated electrons is set as tube current and an irradiation period is set as an exposure period. As an anode (anticathode) into which the electrons crash, copper, molybdenum, rhodium, tungsten or the like can be used, and depending on the kind of the anode, it is possible to change an energy spectrum of irradiated radiation. If copper, molybdenum, rhodium or the like is used as the anode, it is possible to obtain a line spectrum having small range of radiation energy distribution and comparatively low energy, and it is used for mammography where crystal analysis of radiation diffraction and interpretation of minute structure are necessary. If tungsten is used as the anode, it is possible to obtain radiation having a broad spectrum and comparatively high energy, and to use the anode for non-destructive inspection on chest, abdomen and head of a human body, and for industrial purposes. The non-destructive inspection is characteristic of either medical or industrial purposes where large amount of radiation dose is used. In this case, large quantity of electrons crashes into the anode at high speed and it causes high temperature. As a result, there is a possibility of melting the anode due to the high temperature. Therefore, it is necessary to rotate the anode for changing an area into which the electrons crash in order to avoid troubles due to the high temperature. In other words, generally a rotating anode is used. Since the radiation image radiographing apparatus 1 is an apparatus used for either a medical purpose or non-destructive inspection, ideally a radiation tube having a rotating anode made of molybdenum, rhodium or tungsten is used as the radiation source 6.

Here, as shown in FIG. 2, a focal point 7 of radiation irradiated from the radiation source 6 is, for example, a window for taking out radiation generated by crashing the electrons into the rotating anode of the radiation tube, and also a window seen from the subject side. Generally, the window is a square, and length of its side is a focal point size D. If a shape of the window is a circle, its diameter is defined as the focal point size D, and if a shape of the window is a rectangle, its short side is defined as the focal point size D. As a method for measuring the focal point size D, a method with a pinhole camera, a method with a microtest chart and the like are written in JIS Z 4704. Normally, a value of the focal point size D is indicated based on radiation tube manufacturer's measurement as a product specification.

In addition, in order to obtain a sharp image, it is necessary to irradiate radiation more than predetermined amount. Therefore, lower limit of the focal point size D of radiation is determined. Further, in order to obtain a sharp image by optimally achieving emphasis of edges, which are border parts of the subject, caused from radiation inflection, upper limit of the focal point size D is also determined based on a distance between the subject 8 and the radiation image information detecting member, a distance between the focal point 7 and the subject 8, physical property of radiation or the like. Accordingly, in order to perform phase contrast image radiography in a normal medical facility, the focal point size D needs to be within the range from 30 µm to 300 µm, preferably from 30 µm to 200 µm.

As shown in FIG. 1, at both the sides of the radiography unit 44, handles 9 for supporting the body of the examinee are placed. The examinee supports her body by holding the handles 9.

Below the radiography unit 44, a subject platform 10 for supporting the subject 8, which is a mamma of the subject 8, from underneath so as to face the subject 8 to the radiation source 6 is placed. The subject platform 10 is located below the radiation source 6, and within the irradiation field of the radiation irradiated from the radiation source 6. The subject platform 10 is adjusted to have an angle perpendicular to an irradiation direction of the radiation from the radiation source 6. Preferably, the subject platform 10 is either a square frame or a transparent thin plastic plate affixed to a square frame. The subject 8 supported by the subject platform 10 faces the radiation source 6. Here, the case where the subject 8 is a mamma of the examinee is explained However, the subject 8 may be another region of the examinee. Further, the subject is not limited to a human body.

Further, the radiography unit 44 comprises a pressure plate 11. The pressure plate 11 is placed between the radiation source 6 and the subject platform 10 as capable of moving up and down. When the pressure plate 11 moves down while the subject 8 is supported by the subject platform 10, the pressure plate 11 presses the subject 8 from above for fixing it.

Further, the radiography unit 44 comprises a bodyguard 12 at the upper part thereof. The bodyguard 12 extends along the front surface of the upper part of the radiography unit 44 and faces the examinee. With the bodyguard 12, it is possible to minimize radiation exposure on the examinee and prevent from radiographing a part other than the subject 8. The subject platform 10 also comprises a bodyguard 12, and the bodyguard 12 of the subject platform 10 extends along a direction from the front edge of the subject platform 10 downward.

At the lower end of the radiography unit 44, the supporting portion 45 is attached. The supporting portion 45 is fixed in a state of extending along a direction from the lower end of the radiography unit 44 downward.

The supporting platforms 2, 3, 4 and 5 are placed at a side opposite to the radiation source 6 with respect to the subject platform 10, where facing the radiation source 6 within the irradiation field of the radiation from the radiation source 6. The radiation image information detecting members, which are means to detect radiation image information based on the radiation transmitted through the subject 8 supported by the subject platform 10, are respectively attached to the supporting platforms 2, 3, 4 and 5 detachably. The radiation image information detecting member has an area necessary for detecting the radiation transmitted through the subject 8. The radiation irradiated from the radiation source 6 is transmitted through the subject 8 and recorded in the radiation image information detecting member as radiation energy (radiation image information).

When the supporting platforms 2, 3, 4 and 5 are placed as capable of being evacuated from the irradiation field of the radiation from the radiation source 6 and at least one of the supporting platforms 2, 3, 4 and 5 is evacuated from a location where facing the radiation source 6 within the irradiation field of the radiation from the radiation source 6, space is secured at the side opposite to the radiation source 6 with respect to the subject platform 10. In detail, the supporting platforms 2, 3, 4 and 5 are placed as follows.

First, the supporting platform 2 will be explained. A rear anchor part of the supporting platform 2 is attached at the upper part of the supporting portion 45. The supporting platform 2 is placed as capable of rotating from a location where facing the radiation source 6 toward the side opposite to the radiation source 6 with the rear anchor part thereof as a supporting point. In detail, the supporting platform 2 is placed as capable of rotating from a location where the supporting platform 2 lies perpendicular to the irradiation direction from the radiation source 6 and faces the radiation source 6 within the irradiation field of the radiation from the radiation source 6, toward a location where the supporting platform 2 extends from the rear anchor part downward away from the irradiation field.

A rear anchor part of the supporting platform 3 is attached to the supporting portion 45. The supporting platform 3 is placed as capable of rotating with the rear anchor part thereof as a supporting point from a location where the supporting platform 3 faces the radiation source 6 toward the side of the radiation source 6. In detail, the supporting platform 3 is placed as capable of rotating from a location where the supporting platform 3 lies perpendicular to the irradiation direction from the radiation source 6 and faces the radiation source 6 within the irradiation field of the radiation from the radiation source 6, toward a location where the supporting platform 2 stands away from the irradiation field. Thereby, the supporting platform 3 is placed as capable of lying and standing. Here, the attaching location of the rear anchor part of the supporting platform 3 and the supporting portion 45 is located below the attaching location of the rear anchor part of the supporting platform 2 and the supporting portion 45.

A rear anchor part of the supporting platform 4 is attached to the supporting portion 45. The supporting platform 4 is placed as capable of rotating with the rear anchor part as a supporting point from a location where the supporting platform 4 faces the radiation source 6 toward the radiation source 6. In detail, the supporting platform 4 is placed as capable of rotating from a location where the supporting platform 4 lies perpendicular to the irradiation direction from the radiation source 6 and faces the radiation source 6 within the irradiation field of the radiation from the radiation source 6, toward a location where the supporting platform 4 stands away from the irradiation field. Thereby, the supporting platform 4 is placed as capable of lying and standing. Further, the supporting platform 4 is capable of extending and shrinking within a range from a state where the supporting platform 4 extends from its rear anchor part and faces the radiation source 6 to a state where the supporting platform 4 shrinks to its rear anchor part away from the irradiation field. Here, the attaching location of the rear anchor part of the supporting platform 4 and the supporting portion 45 is located below the attaching location of the rear anchor part of the supporting platform 3 and the supporting portion 45. In addition, as well as the supporting platform 4, the supporting platform 3 may be capable of extending and shrinking.

The supporting platform 5 is attached to the lower part of the supporting portion 45 detachably. Thereby, the supporting platform 5 is detachably placed in the apparatus body 40 via the supporting portion 45. When the supporting platform 5 is attached to the supporting portion 45, the supporting platform 5 faces the radiation source 6 as perpendicular to the irradiation direction from the radiation source 6 within the irradiation field of the radiation irradiated from the radiation source 6. When the supporting platform 5 is detached from the supporting portion 45, the supporting platform 5 is capable of being evacuated from a location where facing the radiation source 6 within the irradiation field of the radiation irradiated away from the radiation source 6.

Figure 4:
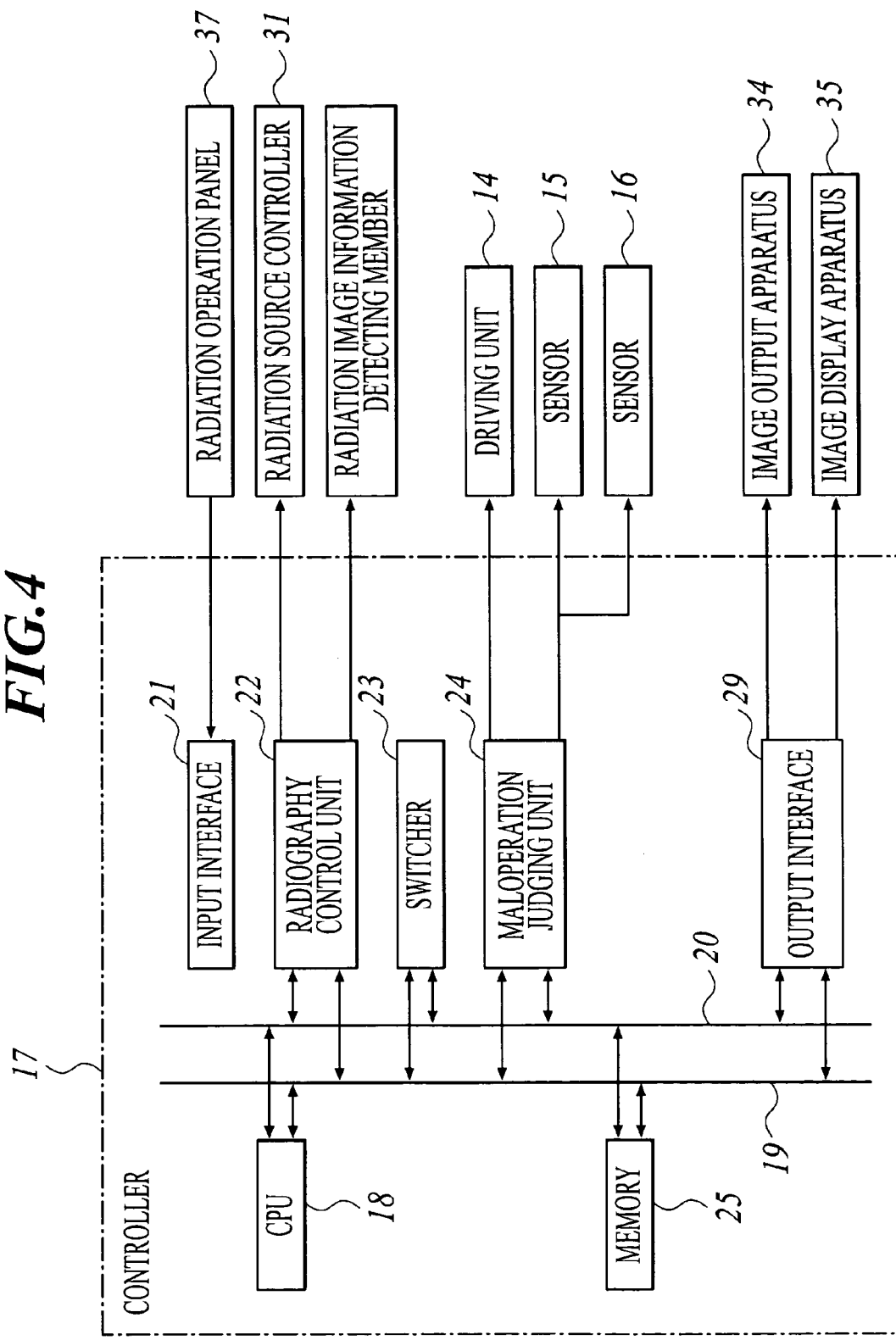
FIG. 4 is a view showing a structure of a controller 17 of the radiation image radiographing apparatus 1.

The supporting platforms 2, 3 and 4 are respectively, when being used, moved to a location where facing the subject platform 10 and, when on standby, evacuated to a location from the irradiation field with their front edge brought to the supporting portion 45 by a driving unit 14 (shown in FIG. 4). In addition, in the present embodiment, a structure where the supporting platforms 2, 3 and 4 are automatically evacuated by the driving unit 14 is explained, but a structure where the supporting platforms 2, 3 and 4 are manually evacuated, is also acceptable.

As mentioned, since the supporting platforms 2, 3 and 4 are capable of lying and standing, it is possible to evacuate the supporting platforms 2, 3 and 4 from the irradiation field without detaching the supporting platforms 2, 3 and 4. In other words, without detaching the supporting platforms 2, 3 and 4, it is possible to evacuate the supporting platforms 2, 3 and 4 to a location where the examinee can be radiographed without any interference. Further, since it is not necessary to detach the supporting platforms 2, 3 and 4, it is not necessary to secure space for the supporting platforms 2, 3 and 4.

Each of the supporting platforms 2, 3, 4 and 5 comprises a sensor 15 for detecting whether each of the supporting platforms 2, 3, 4 and 5 is away from the irradiation field, and a sensor 16 for detecting whether the radiation image information detecting member is attached to each of the supporting platforms 2, 3, 4 and 5 and is usable for radiography.

The plurality of the supporting platforms 2, 3, 4 and 5 are classified into two types, the supporting platform 2 used for radiographing absorption contrast images and the supporting platforms 3, 4 and 5 used for radiographing phase contrast images. In other words, when the supporting platform 2 is placed where facing the radiation source 6 within the irradiation field of the radiation from the radiation source 6, the supporting platform 2 is located where radiography of an absorption contrast image can be performed. Further, when the supporting platforms 3, 4 and 5 are placed where facing the radiation source 6 within the irradiation field of the radiation from the radiation source 6, the supporting platforms 3, 4 and 5 are located where radiography of a phase contrast image can be performed. Further, the radiation image information detecting member supported by the supporting platform 2 is larger than the subject 8.

When the supporting platform 2 for radiographing absorption contrast images is placed where facing the radiation source 6 within the irradiation field of the radiation from the radiation source 6, the supporting platform 2 supports the radiation image information detecting member in contact with the under surface of the subject platform 10. When the supporting platforms 3, 4 and 5 for radiographing phase contrast images are placed where facing the radiation source 6 within the irradiation field of the radiation from the radiation source 6, the supporting platforms 3, 4 and 5 support the radiation image information detecting member with predetermined distance from the subject platform 10 in a state where at least a part of the radiation image information detecting member is located within the irradiation field of the radiation from the radiation source 6.

When the supporting platforms 2, 3, 4 and 5 are placed where facing the radiation source 6 within the irradiation field of the radiation from the radiation source 6, distances from the radiation source 6 to the supporting platforms 2, 3, 4 and 5 are different from each other. For example, the supporting platform 2 is located with distance R1 (distance R1 is 55 cm to 70 cm) below the radiation source 6 and in contact with the under surface of the subject platform 10. Further, the supporting platform 3 is located with distance R2 (distance R2 is 0.5 to 1.5 times as much as the distance R1) below the subject platform 10, the supporting platform 4 is located with distance R3 (distance R3 is 0.3 to 1.0 time as much as the distance R1) below the supporting platform 3, and the supporting platform 5 is located with distance R4 below the supporting platform 4.

The distances from the radiation source 6 to the supporting platform 2, 3, 4 and 5 facing the radiation source 6 are fixed. This is because the supporting platforms 2, 3, 4 and 5 are attached to the supporting portion 45 and the supporting portion 45 is fixedly attached to the lower end of the radiography unit 44.

In addition, in the present embodiment, the supporting platform 2 supports the radiation image information detecting member in contact with the under surface of the subject platform 10. However, as long as the radiation image information detecting member is supported within a range where absorption contrast images can be radiographed at the side opposite to the radiation source 6 with respect to the subject 8, one of the other supporting platforms instead of the supporting platform 2 may support the radiation image information detecting member at any location close to the subject platform 10. For example, one of the other supporting platforms instead of the supporting platform 2 may support it at the upper side or inside of the subject platform 10. Further, the subject platform 10, instead of the supporting platform 2, may support the radiation image information detecting member without having the subject platform 10 and the supporting platform 2 separately.

The radiation image information detecting member comprises a grid to block scattered light from the radiation source 6 for preventing from the scattered light influencing on radiography. However, since the amount of the scattered light and the influence on the radiography could reduce as distance from the subject 8 becomes larger, the radiation image information detecting members supported by the supporting platforms 3, 4 and 5 may not comprise a grid.

As the radiation image information detecting members supported by the supporting platforms 2, 3, 4 and 5:

A. a combination of radiation fluorescent intensifying screen and silver halide photographic film, B. a photostimulable phosphor plate emitting light with photo-stimulation, C. a radiation image information reading apparatus having scintillators for converting radiation energy into light and light semiconductor devices for reading the light, arrayed two-dimensionally, D. a radiation image information reading apparatus having photoconductors for directly converting radiation energy into electric signals and semiconductor devices for reading the electric signals, arrayed two-dimensionally, E. a radiation image information reading apparatus having either a single or a plurality of combinations of scintillators for converting radiation into light and lenses for light-focusing the light to CCD, CMOS or the like arrayed, and F. a radiation image information reading apparatus having scintillators for converting radiation into light and replacing the light with electric signals by leading the light to CCD, CMOS or the like with optical fiber, can be used.

If the radiation image information detecting member supported by the supporting platforms 2, 3, 4 and 5 is the above-mentioned A or B, a radiation dose detector 52 (shown in FIG. 2) may be placed at the backside of each of the supporting platforms 2, 3, 4 and 5. Further, the radiation image information detecting member supported by the supporting platforms 2, 3, 4 and 5 is the so-called flat panel detector such as the above-mentioned C to F and capable of directly taking out radiation energy electrically, the radiation image information detecting member may have the same function as the above-mentioned radiation dose detector 52 without having the radiation dose detector 52.

In the present embodiment, a combination of radiation fluorescent intensifying screen and silver halide photographic film as mentioned in A is also called an SF system (Screen Film system). Radiation fluorescent intensifying screen has rare-earth phosphor such as calcium tungstate, gadolinium oxy-sulphide or the like, and replaces radiation energy with either blue or green luminescence. In particular, regarding intensifying screen using rare-earth phosphor, a technique disclosed in Japanese Patent Application Publication (Unexamined) No. Tokukai-hei 6-67365 may be used. Further, as the silver halide photographic film, preferably the one having either a single or both sides of a supporting body coated with photosensitive emulsion is used. Especially, in the case of using duplicated film, preferably photographic material in which photographic characteristic is different among each of the emulsion layers over the film supporting body is used. Further, preferably, photographic film having a layer for absorbing crossover light placed between each emulsion surface of the duplicated film is used. In the present embodiment, a size of either single-sided and/or duplicated film can be any, from dividing-into-six size to half-dividing size. The silver halide photographic sensitive material is explained in Japanese Patent Application Publication (Unexamined) No. Tokukai-hei 6-67365 or, for example, "Revised Basis of Photography Engineering—Edition of Silver Halide Photography—" (edited by Japan Photography Academic Conference, published by Corona Publishing Co., Ltd.). Further, regarding film processing of the photographic film, although it is possible to improve average tone by raising film processing temperature or extending a time period for the film processing, preferably a film processing condition assigned by a film manufacturer essentially when automatic film processing is done.

With the photostimulable phosphor plate emitting light with photo-stimulation as mentioned in B, by irradiating either infrared light or visible light after radiation is irradiated, visible light luminescence corresponding to intensity of the radiation which already has been irradiated is induced. In other words, the photostimulable phosphor plate emitting light with photo-stimulation is placed as the radiation image information detecting member, and it is moved to a laser reading apparatus or the like for reading emitted light after radiation is irradiated thereon, and by replacing the read light with electric signals by use of an electron multiplier or the like, the electric signals of a radiation image are obtained. The electric signals are, after being applied appropriate image processes on, either displayed on an image display unit such as a monitor or the like, and/or output as hardcopy of the radiation image by use of an image output unit such as a laser imager or the like. At this time, if the image has been magnified, it is possible to either display it on the monitor and/or output as hardcopy by reducing it back to substantially full scale with a predetermined magnifying rate input. As the radiation image information detecting member using the photostimulable phosphor plate, a technique of visualizing images such as phosphor, reading emitted light or the like disclosed in Japanese Patent Application Publication (Laid-open) No. Tokugan-hei 11-49080, can be used in the present embodiment.

Regarding the radiation image information detecting member with a method of converting radiation into electrical signals as mentioned in C to F, techniques disclosed in Japanese Patent Application Publication (Laid-open) No. Tokugan-hei 11-49080 or "Handbook of Medical Imaging" Vol. 1, chapter 4 "Flat panel imagers for digital radiography" (ed. R. V. Matter et al. SPIE Press, Bellingham, 2000) can be used in the present embodiment. In these cases, the radiation image information detecting member may also have a function of the radiation dose detector 52. Thereby, it is possible to appropriately process electric signals obtained from the radiation image information detecting member and either display the image on the monitor and/or output the image as the hardcopy to be used for an image diagnosis.

Figure 3:
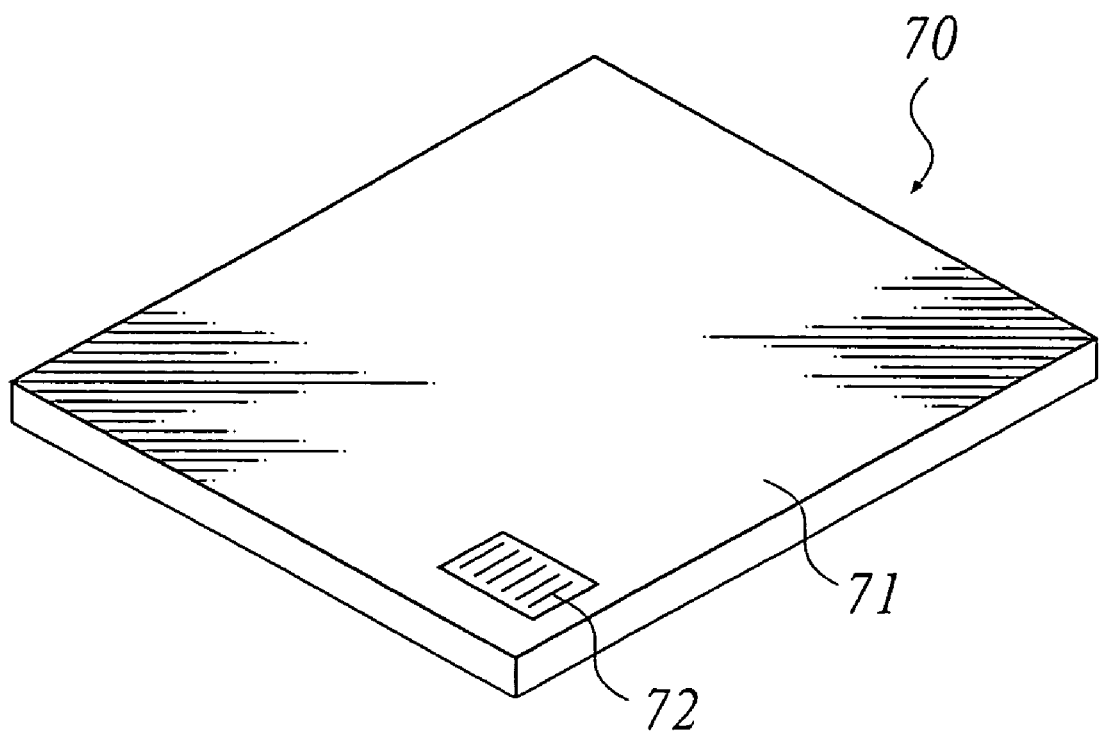
FIG. 3 is a perspective view showing a radiation image information detecting member 70.

FIG. 3 is a perspective view showing a radiation image information detecting member 70, which can be supported by the supporting platforms 2, 3, 4 and 5. The radiation image information detecting member 70 is one example of the radiation image information detecting member which can be supported by the supporting platforms 2, 3, 4 and 5. The radiation image information detecting member 70 is a cassette 71 containing the photostimulable phosphor plate therein. The cassette 71, containing the photostimulable phosphor plate therein, has a thin, box-type shape for avoiding physical damage to the photostimulable phosphor plate when it is carried or used for radiography. In addition, even if only a frame part of the cassette 71 is supported by the supporting platforms 2, 3, 4 and 5, it is possible to maintain its shape for preventing from slipping from a predetermined location. Further, on one side of the cassette 71, a barcode 72, indicating a plate ID number for identifying the photostimulable phosphor plate incorporated therein and/or identification information according to a type of the radiation image information detecting member 70 is labeled. The barcode 72 is capable of being read by a barcode reader placed at the radiation operation panel 37.

Here, if magnified-image radiography in "phase contrast image radiography mode" is performed in order to obtain a phase contrast image, when the obtained radiation image is displayed on a monitor or output on hardcopy such as film or the like, it is possible to automatically reduce its size back to substantially full scale for displaying it.

As the hardcopy, a method for obtaining images by developing with silver halide photosensitive material in an automatic processor; a method for developing with heat after exposure with laser light according to radiation image information despite the use of silver halide photosensitive material; a method for drawing images with heat according to radiation image information and the like are also preferable embodiments. Further, a solid inkjet recording method for drawing images by having nozzles jet heated liquid-state ink, which is solid at room temperature; an inkjet recording method for drawing images by having nozzles jet either dyestuff or pigment, both of which are solid at room temperature; a method for drawing by fixating sublimated ink ribbon with heat on recording medium; an abrasion image forming method for drawing images by evaporating sheet which is entirely covered with carbon and the like with heat of laser light based on image information may be used as the hardcopy.

Next, with reference to FIG. 4, a structure of a controller 17 of the radiation image radiographing apparatus 1 in the present embodiment will be explained.

In the present embodiment, to a CPU (Central Processing Unit) 18 controlling the whole operation of the controller 17, a system bus 19, an image bus 20 and an input interface 21 are connected. To the system bus 19 and the image bus 20, a radiography control unit 22, a switcher 23, a maloperation judging unit 24, a memory 25 and an output interface 29 are connected.

To the input interface 21, the radiation operation panel 37 is connected as an input device for inputting a radiography mode. On the radiation operation panel 37, keys to select "absorption contrast image radiography mode" for performing radiography with the radiation image information detecting member attached to the supporting platform 2; "first phase contrast image radiography mode" for performing radiography with the radiation image information detecting member attached to the supporting platform 3; "second phase contrast image radiography mode" for performing radiography with the radiation image information detecting member attached to the supporting platform 4; and "third phase contrast image radiography mode" for performing radiography with the radiation image information detecting member attached to the supporting platform 5 are placed. With the keys placed on the radiation operation panel 37, it is possible to selectively input one of the absorption contrast image radiography mode and the phase contrast image radiography modes having different magnifying rates corresponding to the supporting platforms 2, 3, 4 and 5, respectively. Further, as the input device, an input device using a keyboard, a magnetic card, a barcode, an HIS (Hospital Information System) or the like may be used instead of the radiation operation panel 37.

Further, to the radiography control unit 22, a radiation source controller 31 for controlling an irradiation condition of the radiation source 6 is connected. In addition, if the radiation image information detecting member to be used for radiography is a type of converting radiation into electric signals, the radiation image information detecting member is connected to the radiography control unit 22 so as to appropriately process the electric signals of the obtained radiation image and transmit them to the radiography control unit 22.

Further, an output interface 29 is connected to an image output apparatus 34 for outputting images obtained from radiography to a printer or the like, and an image display apparatus 35 for displaying the image on a display.

Next, with reference to FIG. 4, a concrete procedure of a radiographing method by use of the radiation image radiographing apparatus 1 in the present embodiment will be explained.

First, an operator attaches the radiation image information detecting member to any one of the supporting platforms 2, 3, 4 and 5 (one corresponding to a radiography mode to be performed by the operator). Then, when the operator selects a radiography mode by operating the keys placed on the radiation operation panel 37, information of the selected radiography mode is transmitted as electric signals to the CPU 18 in the controller 17 contained in the first supporting base 41 via the input interface 21.

The CPU 18, in response to the information of the selected radiography mode, transmits a radiography condition indicating whether the absorption contrast image radiography or the phase contrast image radiography is to be performed to the radiography control unit 22 and the switcher 23. The switcher 23, in response to the electric signals of the radiography condition, makes an instruction of switching among "first phase contrast image radiography mode", "second phase contrast image radiography mode", "third phase contrast image radiography mode" and "absorption contrast image radiography mode". Here, an input of the radiography condition and the like may be done, by selecting one of the keys placed on the radiation operation panel 37 as mentioned; at the input device placed instead of the radiation operation panel 37; or by automatically recognizing a radiography mode with the sensors 15 and 16 placed at each of the supporting platforms 2, 3, 4 and 5. Concretely, when the operator selects a predetermined key on the radiation operation panel 37 for inputting a radiography mode, the switcher 23 makes the switching instruction in response to the input. Further, if a radiography mode is automatically recognized with the sensors 15 and 16 placed at each of the supporting platforms 2, 3, 4 and 5, the sensor 15 detects whether each of the supporting platforms 2, 3, 4 and 5 is at a location where radiography can be performed or out of the irradiation field, as well as the sensor 16 detects whether the radiation image information detecting member is attached to each of the supporting platforms 2, 3, 4 and 5 and is usable for radiography. Then, information of the automatic recognition is transmitted to the switcher 23 as electric signals, and the switcher 23 makes the switching instruction. Further, when the radiography condition is transmitted to the radiography control unit 22, the radiation source controller 31 controls the irradiation condition of radiation according to the transmitted radiography condition.

Here, a control procedure in the case where the switching instruction is transmitted will be explained.

If the operator inputs the key of "absorption contrast image radiography mode" among the keys placed on the radiation operation panel 37, the controller 17 activates the driving unit 14 for rotating the supporting platforms 2, 3 and 4. Hereby, the supporting platform 2 is placed where facing the radiation source 6 within the irradiation field of the radiation from the radiation source 6 and the radiation image information detecting member supported by the supporting platform 2 is contacted to the under surface of the subject platform 10. The supporting platforms 3 and 4 stand at a location away from the irradiation field. Regarding the supporting platform 4, when the front edge thereof is located close to the supporting portion 45, the operator slides the supporting platform 4 to shrink it, and when the operator needs to put the radiation image information detecting member on the supporting platform 4, the operator slides the supporting platform 4 to extend it. In addition, in the case of "absorption contrast image radiography mode", the operator detaches the supporting platform 5 from the supporting portion 45 in advance.

Thereafter, the examinee puts the subject 8 on the subject platform 10, the controller 17 lowers the pressure plate 11 to press the subject 8. Then, the controller 17 transmits an instruction of the irradiation condition of radiation and the like to the radiography control unit 22, the controller 17 controls the radiography condition according to the instruction. Thereby, the radiation source 6 irradiates radiation for performing radiography. At this time, for example, if the operator inputs a radiography condition corresponding to sensitivity of intensifying screen MD-100 (made by Konica) and single-sided film for mammography CMH (made by Konica) in advance, the controller 17 automatically sets the irradiation conditions such as 28 kVp, 12 mA, 1.2 seconds and the like, and controls the radiation source controller 31 to make a state of radiography "ON" for performing the absorption contrast image radiography.

On the other hands, the operator inputs one of the keys of "first phase contrast image radiography mode", "second phase contrast image radiography mode" and "third phase contrast image radiography mode" placed on the radiation operation panel 37, the controller 17 transmits an instruction of the irradiation condition and the like to the radiography control unit 22 for performing radiography with the radiation image information detecting member attached to a supporting platform corresponding to the input mode among the supporting platforms 3, 4 and 5. Further, the radiography control unit 22, in response to the switching instruction from the switcher 23, obtains the location information of each of the supporting platforms 2, 3, 4 and 5 based on information of recognition of the sensors 15 and 16 placed at each of the supporting platforms 2, 3, 4 and 5. If any one of the supporting platforms 2, 3 and 4 is located where it could interfere radiography, the driving unit 14 evacuates the one interfering radiography among the supporting platforms 2, 3 and 4 away from the irradiation field.

Concretely, when "first phase contrast image radiography mode" is selected, the controller 17 activates the driving unit 14 for rotating the supporting platforms 2, 3 and 4. The supporting platform 3 is placed where facing the radiation source 6 within the irradiation field of the radiation from the radiation source 6, the supporting platform 2 is evacuated from the irradiation field downward, and the supporting platform 4 stands away from the irradiation field. When "second phase contrast image radiography mode" is selected, the controller 17 activates the driving unit 14 for rotating the supporting platforms 2, 3 and 4. The supporting platform 4 is placed where facing the radiation source 6 within the irradiation field of the radiation from the radiation source 6, the supporting platform 2 is evacuated from the irradiation field downward, and the supporting platform 3 stands away from the irradiation field. When "third phase contrast image radiography mode" is selected, the controller 17 activates the driving unit 14 for rotating the supporting platforms 2, 3 and 4. The supporting platform 2 is evacuated from the irradiation field downward, and the supporting platforms 3 and 4 stand away from the irradiation field. Further, in the case of "first phase contrast image radiography mode" or "second phase contrast image radiography mode", the operator detaches the supporting platform 5 from the supporting portion 45. In the case of "third phase contrast image radiography mode", the operator attaches the supporting platform 5 to the supporting portion 45 in advance for placing the supporting platform 5 within the irradiation field as facing the radiation source 6.

Thereafter, when the examinee puts the subject 8 on the subject platform 10, the controller 17 lowers the pressure plate 11 to press the subject 8. Then, the controller 17 controls the radiography condition according to the irradiation condition and the like, and the radiation source 6 irradiates radiation for performing radiation image radiographing. At this time, if the operator inputs a radiography condition corresponding to sensitivity of, for example, XGM back intensifying screen (made by Konica) and single-sided film for mammography CMH (made by Konica), in other words, irradiation conditions such as 28 kVp, 16 mA, 2-second exposure and the like in advance, the controller 17 automatically sets the condition and controls the radiation source controller 31 to make a state of radiography "ON" for performing phase contrast image radiography.

At this time, information regarding a radiography mode, the radiography condition and the like along with the examinee information of the subject 8 are recorded in film by use of the controller 17, and after the film developing process, a mammography image is obtained. Further, in addition to an output on the film, the photostimulable phosphor plate emitting stimulated light or the like can be used as the radiation image information detecting member. For example, Konica's REGIUS plate RP-1S (dividing-into-four size) is used as the photostimulable phosphor plate emitting stimulated light, and Konica's REGIUS MODEL 150 reads the image from it after the radiography. Then, after appropriate image process is applied on the image, it is possible to display the image on the image display apparatus 35 such as a monitor or the like, or obtain hardcopy of the obtained radiation image information by use of the image output apparatus 34 such as a laser imager or the like.

In addition, when radiography is performed in one of "first phase contrast image radiography mode", "second phase contrast image radiography mode" and "third phase contrast image radiography mode", since the radiation image information detecting member is distanced from the subject 8, a magnified image of the subject 8 is obtained with the radiography. Thereby, the image can be displayed on the image display apparatus 35 or output at the image output apparatus 34 with either the magnifying rate of the image kept or the size of the image reduced back to substantially full scale based on the magnifying rate (a magnifying rate compared to the subject 8 at full scale) at the time of the radiography.

Further, in the case of either having the radiation dose detector 52 as a means to detect radiation or the radiation image information detecting member functioning as the radiation dose detector 52, when electric signals of radiation intensity information obtained from the radiation image information detecting member are input to the radiation dose detector 52, in consideration of information of the electric signals, sensitivity of the radiation image information detecting member, radiation tube programmed voltage and the like, a radiography condition is calculated with focal point diameter information, a control program and the like stored in the memory 25 in advance. Accordingly, the controller 17 controls the radiation source controller 31, and the irradiation condition of radiation for radiography by use of the radiation source controller 31.

Here, the case where the irradiation condition of radiation and the supporting platforms 2, 3, 4 and 5 are automatically controlled by inputting the radiography condition is explained as above. However, settings of the irradiation condition and/or selection of one of the supporting platforms 2, 3, 4 and 5 may be made manually.

Further, the CPU 18 transmits signals regarding the apparatus transiting a radiography-capable state and radiography mode information to the maloperation judging unit 24. The maloperation judging unit 24, in response to the signals, for example, recognizes each location of the supporting platforms 2, 3, 4 and 5 and whether the radiation image information detecting member is attached to each of the supporting platforms 2, 3, 4 and 5 with the sensors 15 and 16. Then, if the radiation image information detecting member is not attached to a supporting platform to be used for the selected radiography mode among the supporting platforms 2, 3, 4 and 5, or if more than one radiation image information detecting member are in a state usable for radiography, the CPU 18 warns with a buzzer or the like. In this case, for example, if the radiation image information detecting member attached to the supporting platform 2 is judged as usable for radiography while it is necessary to perform radiography with the radiation image information detecting member attached to either the supporting platform 3 or 4, it is possible to eliminate the maloperation state and cancel the warning by getting rid of the grid attached to the supporting platform 2 for leaving the subject platform 10 alone. Further, if the radiation image information detecting member attached to the supporting platform 3 is judged as usable for radiography while it is necessary to perform radiography with the radiation image information detecting member attached to the supporting platform 4, similarly it is possible to cancel the warning by rotating the supporting platform 3 from the irradiation field by use of the driving unit 14.

Here, the case of controlling the supporting platforms 2, 3 and 4 interfering radiography to be automatically evacuated when the CPU 18 warns for preventing maloperation is explained as above. However, the supporting platforms 2, 3, 4 and 5 may be evacuated manually.

As mentioned above, in the present embodiment, since the supporting platforms 2, 3, 4 and 5 are respectively placed and fixed where the distances from the radiation source 6 are different depending on the supporting platforms 2, 3, 4 and 5, when it is necessary to switch a radiography mode, it is only necessary to select one of the radiation image information detecting members attached to the supporting platforms 2, 3, 4 and 5. Thereby, the operator does not have to adjust a magnifying rate for himself whereas he would have to do in an earlier art. Therefore, it is possible to switch a radiography mode easily, and improve user-friendliness compared to the earlier art.

Further, since it is possible to select a radiation image information detecting member with an easy method such as attaching the radiation image information detecting member to any one of the predetermined supporting platforms 2, 3, 4 and 5 or the like, it is possible to switch the radiography mode corresponding to each of the supporting platforms 2, 3, 4 and 5 among "absorption contrast image radiography mode", "first phase contrast image radiography mode", "second phase contrast image radiography mode" and "third phase contrast image radiography mode". Thereby, it is possible to improve user-friendliness, simplify the apparatus and reduce cost.

Further, in the present embodiment, there is a means to reduce a size an image radiographed in a magnifying mode back to substantially full scale. Here, an image at substantially full scale reduced from an image once radiographed in the magnifying mode can have higher spatial resolution than an image radiographed at substantially full scale. Further, when it is necessary to do the image diagnosis, since it is necessary to have accurate understanding on a circumstance of a diagnostic region, it is possible to diagnose an image more accurately at substantially full scale. Accordingly, when an image is radiographed in the magnifying mode, it is possible not only to use the radiographed image as a magnified image, but also to obtain an image with high spatial resolution by reducing its size.

Further, according to the present embodiment, in the case of "absorption contrast image radiography mode", that is, radiographing an absorption contrast image, the front edges of the supporting platforms 3 and 4 are evacuated close to the supporting portion 45 so as to secure space at the side opposite to the radiation source 6 with respect to the subject platform 10, and the operator detaches the supporting platform 5 for evacuating it. Thereby, it is possible to prevent from the supporting platforms 3, 4 and 5 interfering the examinee. As a result, it is possible to radiograph an absorption contrast image while the examinee stays seated on a chair such as a wheelchair. Consequently, it is possible to reduce a burden on the examinee.

Further, when it is necessary to radiograph an absorption contrast image, if the supporting platforms 3, 4 and 5 are evacuated from the irradiation field of the radiation source 6, while the radiation image information detecting members remain attached to the supporting platforms 3, 4 and 5, the radiation source 6 does not irradiate radiation on the attached radiation image information detecting members. For example, if a radiation image information detecting member having silver halide photographic film is used, it is possible to prevent from wasting the silver halide photographic film. Further, when it is necessary to radiograph an absorption contrast image, if the radiation image information detecting member is detached, while the supporting platforms 3, 4 and 5 are not evacuated from the irradiation field of the radiation source 6, the radiation source 6 does not irradiate radiation on the radiation image information detecting member. For example, if a radiation image information detecting member having silver halide photographic film is used, it is possible to prevent from wasting the silver halide photographic film.

In addition, the present invention is not limited to the above-mentioned embodiment, and can be changed accordingly, of course.

For example, in the above-mentioned embodiment, the structure where the supporting portion 45 is fixed on the radiography unit 44, the supporting platforms 2, 3, 4 and 5 vertically move along the irradiation direction of the radiation from radiation source 6 along with the radiation source 6 and the subject platform 10, and the supporting platform 3, 4 and 5 are not capable of approaching the subject platform 10 is explained. On the other hand, if the supporting portion 45 is placed as capable of moving vertically along the radiography unit 44, the supporting platforms 2, 3, 4 and 5 vertically move separately from the radiation source 6 and the subject platform 10. Further, if the supporting platform 3 is capable of being in contact with the subject platform 10, it is possible to detect radiation on the radiation image information detecting member supported by the supporting platform 3 at the time of radiographing not only a phase contrast image but also an absorption contrast image. In addition, a structure where the radiography unit 44 is capable of housing the supporting platforms 3 and 4 at the time of radiographing an absorption contrast image, by folding the supporting platforms 3 and 4 to a location parallel to the supporting portion 45 and lifting the supporting portion 45, may be used.

Further, in the above-mentioned embodiment, the supporting platforms 3 and 4 are capable of lying and standing. However, even if the supporting platforms 3 and 4 are not capable of lying and standing, with the supporting platforms 3 and 4 attached to the supporting portion 45 either detachably and/or as capable of extending and shrinking, the supporting platforms 3 and 4 is capable of moving. If the supporting platforms 3 and 4 are capable of extending and shrinking, when the supporting platforms 3 and 4 are extended, the radiation image information detecting member can be placed within the irradiation field of the radiation source 6, and when the supporting platforms 3 and 4 are shrunk, the radiation image information detecting member does not interfere the examinee. Further, a structure where the supporting platforms 3, 4 and 5 are capable of lying and standing, and also either capable of being attached to and being detached from the supporting portion 45 and/or extending and shrinking may be applicable.

Further, a structure where the supporting portion 45 itself is detachable from the apparatus body 40 so as to evacuate the supporting platforms 2, 3, 4 and 5 in order to eliminate the interference to the examinee, may be applicable.

Second Embodiment

Hereinafter, with reference to figures, a second embodiment applied to the present invention will be explained.

Figure 5:
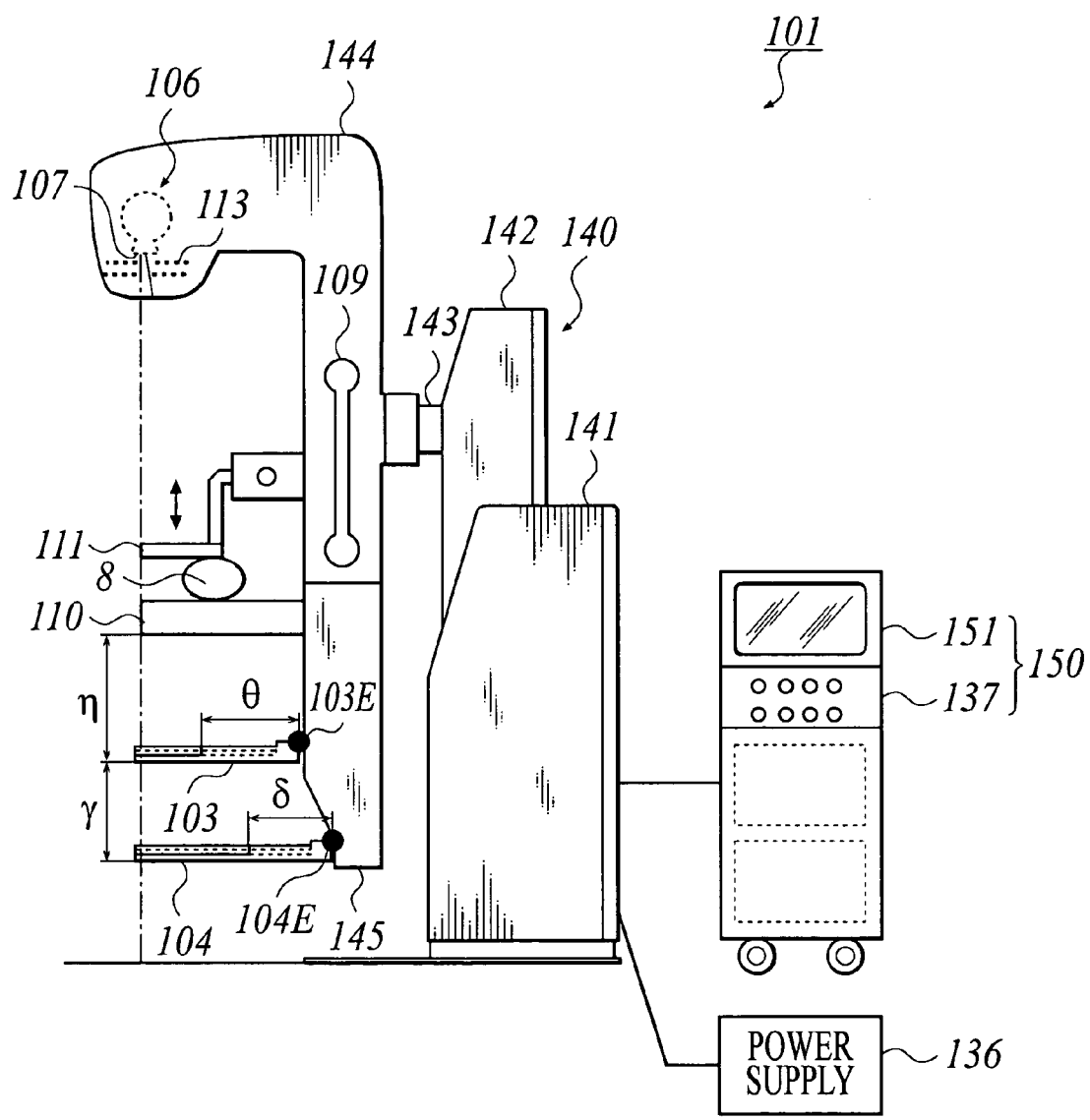
FIG. 5 is a side view showing a radiation image radiographing apparatus 101 in a second embodiment applied to the present invention.

FIG. 5 is a side view showing a radiation image radiographing apparatus 101 in the second embodiment applied to the present invention. As shown in FIG. 5, in the radiation image radiographing apparatus 101, to each part, a code having lower two digits equal to the corresponding part in the radiation image radiographing apparatus 1 in the first embodiment is distributed.

As shown in FIG. 5, the radiation image radiographing apparatus 101, as well as the radiation image radiographing apparatus 1, comprises an apparatus body 140, a radiation operation panel 137, a power supply 136, supporting platforms 103 and 104, and a supporting member 145.

The apparatus body 140 has a first supporting base 141, a second supporting base 142, a spindle 143 and a radiography unit 144. To the first supporting base 141, an operation device 150 having the radiation operation panel 137 such as a keyboard or the like for inputting a radiography condition or the like, and a display unit 151 such as a liquid crystal display or the like for displaying various types of messages, and the power supply 136 as a power source are connected.

Further, the second supporting base 142 is capable of moving vertically along the first supporting base 141. The radiography unit 144 is supported by the second supporting base 142 as capable of rotating around the spindle 143.

At the upper part of the radiography unit 144, a radiation source 106 is placed for irradiating radiation. The radiation source 106 is connected to the power supply 136, and the power supply 136 impresses tube voltage to the radiation source 106. At an irradiation gate of the radiation source 106, a window of an aperture 113 for adjusting irradiation field is placed as capable of opening and shutting.

At the lower part of the radiography unit 144, a subject platform 110 for supporting the subject 8 is placed so as to face the subject 8 to the radiation source 106. The subject platform 110 is located within the irradiation field of radiation irradiated from the radiation source 106, and its angle is adjusted so as to be perpendicular to an irradiation direction of the radiation.

Further, in the radiography unit 144, a pressure plate 111 is placed as capable of moving up and down so as to press the subject 8 on the subject platform 110 for fixing it from above.

Further, handles 109 for supporting the body of the examinee are placed at both sides of the radiography unit 144.

At the lower part of the radiography unit 144, a supporting portion 145 is placed. At the supporting portion 145, two supporting platforms 103 and 104 for supporting radiation image information detecting members for radiographing a phase contrast image of the subject 8 at a side opposite to the radiation source 106 with respect to the subject platform 110 are placed where facing the radiation source 106 within the irradiation field of the radiation irradiated from the radiation source 106.

Figure 6A:
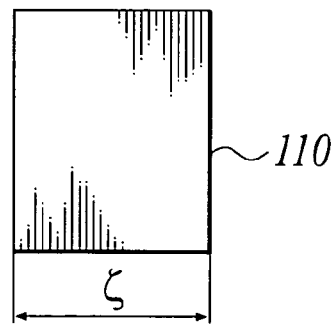
FIG. 6A is a plan view showing a subject platform 110.
Figure 6B:
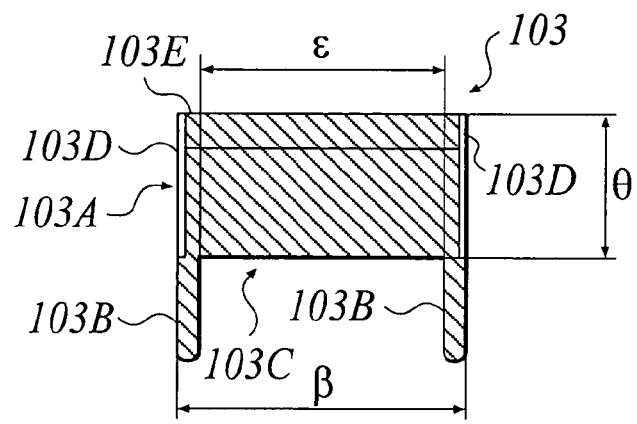
FIG. 6B is a plan view showing a supporting platform 103.
Figure 6C:
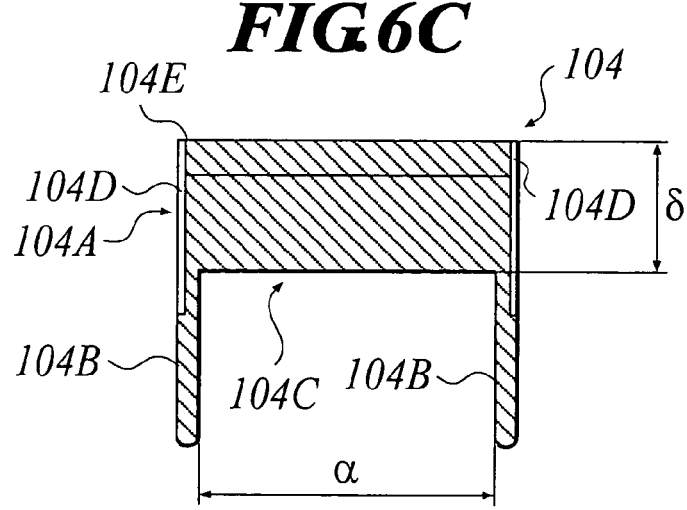
FIG. 6C is a plan view showing a supporting platform 104.

FIG. 6A is a plan view showing the subject platform 110, FIG. 6B is a plan view showing the supporting platform 103 and FIG. 6C is a plan view showing the supporting platform 104. In FIG. 6A, FIG. 6B and FIG. 6C, the upper side of each of the figures corresponds to the side of the supporting portion 145. In FIG. 6B and FIG. 6C, where parallel diagonal lines are drawn indicates areas for supporting the radiation image information member. As shown in FIG. 6B, the supporting platform 103 comprises a rectangular-shape supporting platform body 103A, and projection parts 103B placed on the same plane of the supporting platform body 103A. Further, the supporting platform body 103A and the projection parts 103B together form the supporting platform 103 as a U-shape, thus, between the projection parts 103B, a cut portion 103C is secured. Thereby, the supporting platform 103 supports a frame part of the radiation image information detecting member. Further, at the upper part of the supporting platform 103, guide portions 103D are placed for guiding a position of the radiation image information detecting member. As shown in FIG. 6C, the supporting platform 104, comprises a supporting platform body 104A and projection parts 1048, and forms a U-shape with a cut portion 104C secured between the projection parts 1048 for supporting the frame part of the radiation image information detecting member. At the upper part of the supporting platform body 104A, guide portions 104D are placed.

Figure 7:
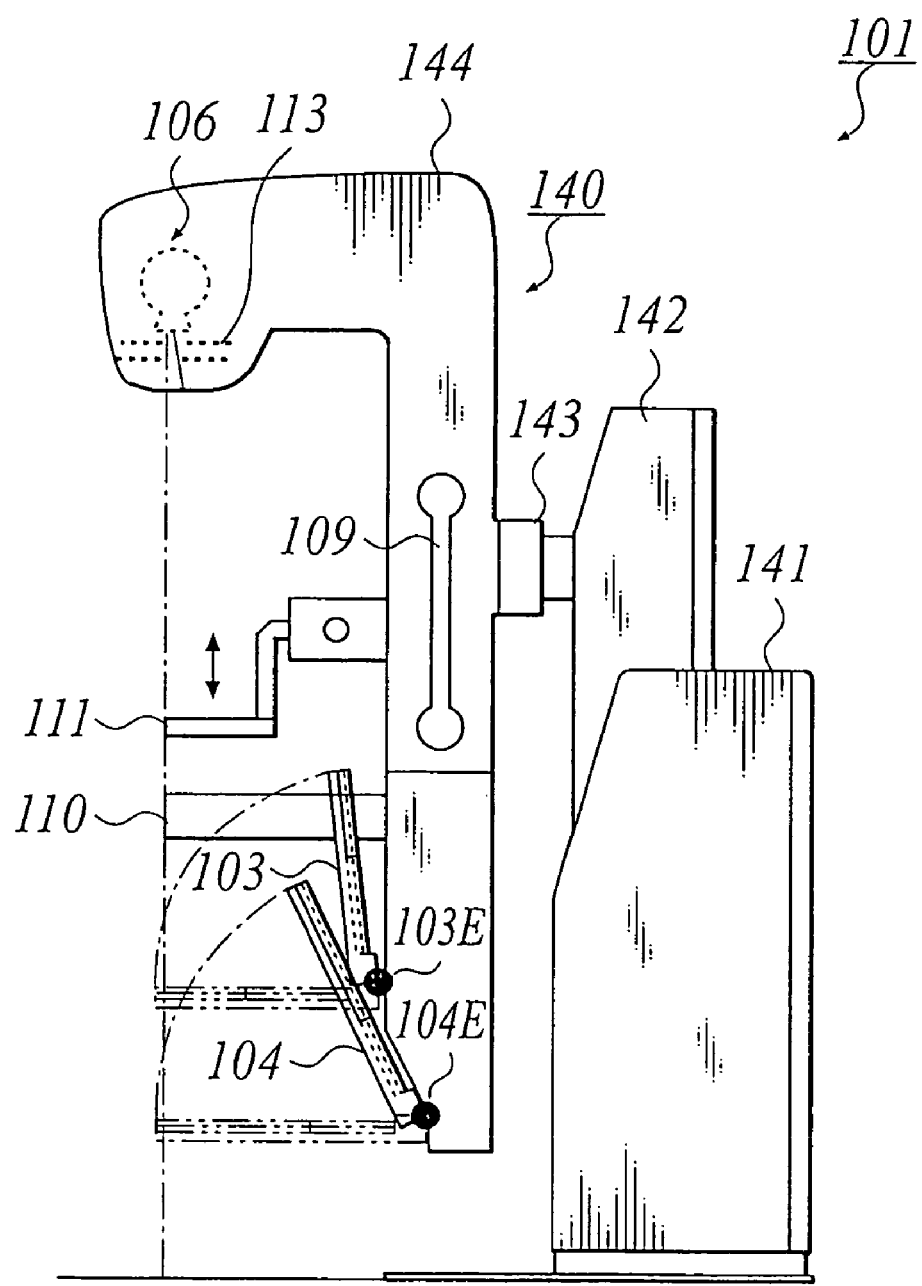
FIG. 7 is a view showing a state where the supporting platforms 103 and 104 are evacuated.

Further, a rear anchor 103E of the supporting platform 103 is attached to the intermediate part of the supporting portion 145 in a vertical direction, and a rear anchor 104E of the supporting platform 104 is attached to the lower part of the supporting portion 145. Further, as shown in FIG. 7, the supporting platforms 103 and 104 are respectively capable of rotating from positions where radiography can be performed shown as chained lines in FIG. 2 (positions where the supporting platforms 103 and 104 lie perpendicular to the irradiation direction of the radiation from the radiation source 106 within the irradiation field and face the radiation source 106) toward the radiation source 106 with the rear anchors 103E and 104E as supporting points. When the supporting platforms 103 and 104 rotate from the positions where radiography can be performed toward the radiation source 106, the supporting platforms 103 and 104 stand away from the irradiation field.

When the supporting platforms 103 and 104 are placed where facing the radiation source 106 within the irradiation field, distances from the supporting platforms 103 and 104 to the radiation source 106 are different from each other. Further, when the supporting platforms 103 and 104 are placed where facing the radiation source 106 within the irradiation field, the supporting platforms 103 and 104 are placed where a phase contrast image can be radiographed. Accordingly, the supporting platforms 103 and 104 are platforms for radiographing a phase contrast image.

As shown in FIG. 6A, FIG. 6B and FIG. 6C, sizes of the supporting platforms 103 and 104 gradually decrease as they are placed closer to the radiation source 106, and are larger than the size of the radiation source 106. Concretely, width $\beta$ of the supporting platform 103 is wider than width $\zeta$ of the subject platform 110, but smaller than width of the supporting platform 104. Thereby, a size of a radiation image information detecting member supported by the supporting platform 103 is wider than the size of the subject 8, but smaller than the size of a radiation image information detecting member supported by the supporting platform 104.

Further, width a of the cut portion 104C of the supporting platform 104 is wider than the width $\beta$ of the supporting platform 103, and width e of the cut portion 103C of the supporting platform 103 is wider than the width $\zeta$ of the subject platform 110.

Further, as shown in FIG. 5, an interval $\eta$ between the subject platform 110 and the supporting platform 103 is wider than width $\theta$ of the supporting platform body 103A (refer to FIG. 6B), and an interval $\gamma$ between the supporting platform 103 and the supporting platform 104 is wider than width $\delta$ of the supporting platform body 104A (refer to FIG. 6C).

In addition, preferably, distances from the supporting platforms 103 and 104 to a radiation tube focal point 107 are within the range from 105 cm to 150 cm for obtaining high-contrast, high-quality radiation images.

In the second embodiment, the radiation image information detecting member capable of being supported by the supporting platforms 103 and 104 is the same as the radiation image information detecting member used in the first embodiment. For example, the radiation image information detecting member 70 shown in FIG. 3 can be used.

Further, at the under surfaces of the supporting platforms 103 and 104, a radiation dose detector for detecting intensity of irradiated radiation dose is placed. The radiation dose detector makes the radiation source 106 stop irradiating radiation when radiation dose transmitted through the subject 8 reaches predetermined amount.

Here, in order to obtain a phase contrast image having high contrast of the subject 8 by use of a phase lag caused when the radiation is transmitted through the subject 8, it is necessary to have an interval no less than 75 cm between the radiation tube focal point 107 of the radiation source 106 and the radiation image information detecting member, and an interval no less than 15 cm between the subject platform 110 and the radiation image information detecting member.

In addition, the wider the interval between the subject platform 110 and the radiation image information detecting member is, the bigger an edge effect from the phase contrast becomes. However, if this interval is too wide compared to an interval between the radiation tube focal point 107 and the subject platform 110, sharpness of the image decreases due to the blur of half shadow. Therefore, preferably both the intervals between the subject platform 110 and the radiation image information detecting member and between the radiation tube focal point 107 and the subject platform 110 are wide in view of improving image quality. On the other hand, if those intervals are wide, the whole size of the radiation image radiographing apparatus 101 also becomes large. Therefore, it is problematic in view of a size of the radiography room and convenience of managing the radiation image radiographing apparatus 101.

From the above-mentioned views, for obtaining a phase contrast image, preferably it is necessary to control the positions of the supporting platforms 103 and 104 for having the interval between the radiation tube focal point 107 and the radiation image information detecting member no less than 85 cm. On the other hand, in view of convenience of managing the apparatus, preferably it is necessary to determine the positions of the supporting platforms 103 and 104 for having the interval between the radiation tube focal point 107 and the radiation image information detecting member no more than 200 cm. Accordingly, preferably the interval between the subject platform 110 and the radiation tube focal point 107 is within the range from 50 cm to 100 cm and the interval between the subject platform 110 and the radiation image information detecting member is within the range from 15 cm to 100 cm for obtaining a good-quality image. In addition, more preferably, the interval between the radiation tube focal point 107 and the radiation image information detecting member is within the range from 90 cm to 165 cm, the interval between the radiation tube focal point 107 and the subject platform 110 is within the range from 60 cm to 75 cm, and the intervals between the subject platform 110 and the supporting platforms 103 and 104 are within the range from 30 cm to 90 cm.

Here, the radiation source 106 in the present embodiment will be explained.

In the present embodiment, as the radiation source 106, a radiation tube irradiating radiation with wavelength from 0.01 nm to 0.1 nm is used. In the radiation tube, electrons generated with thermal excitation are accelerated by high voltage to crash into an anode, and its kinetic energy is converted into irradiation energy for irradiating radiation. When radiation images are radiographed, its acceleration voltage is set as tube voltage, and numbers of generated electrons are set as tube current, and an irradiation period is set as an exposure period. As the anode (anticathode) into which the electrons crash, copper, molybdenum, rhodium, tungsten or the like can be used, and by changing its type, it is possible to change energy spectra of the radiation irradiated. If copper, molybdenum, rhodium or the like is used as the anode, it is possible to obtain line spectrum having small range of radiation energy distribution and comparatively low energy, and it is used for mammography where crystal analysis of radiation diffraction and interpretation of minute structure are necessary. If tungsten is used as the anode, it is possible to obtain radiation having broad spectrum and comparatively high energy, and use the anode for non-destructive inspection on chest, abdomen and head of a human body, and for industrial purposes. The non-destructive inspection is characteristic of either medical or industrial purposes when large amount of radiation dose is used. In this case, large quantity of electrons crashes into the anode at high speed and causes high temperature. As a result, there is a possibility of melting the anode due to the high temperature. Therefore, it is necessary to rotate the anode for changing an area into which the electrons crash in order to avoid troubles due to the high temperature. In other words, generally a rotating anode is used. Since the radiation image radiographing apparatus used in the present embodiment is an apparatus used for either a medical purpose or non destructive inspection, preferably a radiation tube having a rotating anode made of molybdenum, rhodium or tungsten is used, more preferably, since the radiation image radiographing apparatus 101 is used for mammography, the rotating anode is made of molybdenum or rhodium.

Here, the focal point 107 of the radiation source 106 is, for example, a window for taking out radiation generated with the electrons crashed into the rotating anode of the radiation tube, and is also a window seen in a direction from the subject. Generally, the window is a square, and length of its side is defined as a focal point size. If the shape of the window is a circle, its diameter is defined as the focal point size, and if the shape of the window is a rectangle, its short side is defined as the focal point size. As a measurement method of the focal point size, a method with a pinhole camera, a method with a microtest chart and the like are written in JIS Z 4704. Normally, a value of the focal point size is indicated based on radiation tube manufacturer's measurement as product specification.

Further, if a focal point size of the radiation source 106 is large, more mount of radiation is irradiated. Accordingly, the so-called half shadow is caused. The half shadow is a phenomenon where one point of the subject is detected on the radiation image information detecting member as an image having a certain scale due to the size of the focal point 107, that is, blur. Therefore, if the radiation source 106 is a radiation source having a small focus, since it has the limited size of the focal point, influence of the half shadow is problematic unlike the case of synchrotron where monochromatic parallel radiation is output or the case of a micro focus radiation source which can be regarded as a point of focus. Then, width of the blur caused by the half shadow increases as the interval between the subject 8 and the radiation image information detecting member becomes wider.

Therefore, in order to prevent the blur of the half shadow and obtain an image with high sharpness in phase contrast image radiography, upper limit of the focal point size is determined according to the interval between the subject 8 and the radiation image information detecting member, the interval between the radiation source 106 and the subject 8, radiation physical property or the like. On the other hand, in order to obtain radiation dose more than predetermined amount, since it is necessary to have the focal point size more than a predetermined size, lower limit of the focal point size is determined.

As a result, in order to perform phase contrast radiography in a general medical facility, preferably the focal point size is within the range from 30 µm to 300 µm, more preferably the range from 50 µm to 200 µm.

Next, a concrete procedure of a radiographing method by use of the radiation image radiographing apparatus 101 will be explained. Here, in the present embodiment, a structure where phase contrast image radiography is performed with the supporting platform 104, will be explained. However, a case where phase contrast image radiography is performed with the supporting platform 103, may be applied to the structure hereafter.

First, the operator attaches the radiation image information detecting member to the supporting platform 104 and rotates the unused supporting platform 103 upward. At this time, since the width β of the cut portion 103C of the supporting platform 103 is wider than the width ζ of the subject platform 110, and the interval η between the subject platform 110 and the supporting platform 103 is wider than the width θ of the supporting platform body 103A, at least a part of the subject platform 110 passes through the cut portion 103C. Thereby, the supporting platform 103 is rotated without interference from the subject platform 110 and evacuated from space below the subject platform 110.

In this state, when the examinee puts the subject 8 on a predetermined position of the subject platform 110 while holding handles 109, the pressure plate 111 moves down to press and fix the subject 8 on the subject platform 110. Then, the radiation source 106 irradiates radiation. Herewith, radiography of the subject 8 starts, and a radiation image is formed from the radiation transmitted through the subject 8 in the radiation image information detecting member.

According to the radiation image radiographing apparatus 101 as mentioned above, it is possible to prevent from the supporting platform 103 interfering the examinee by rotating the supporting platform 103, which could interfere the radiography, to evacuate it from the space below the subject platform 110. Therefore, compared to the case where supporting platforms are placed in a state of moving up and down, stretching, detachable or foldable, it is possible to easily evacuate the unused supporting platform 103 with operator's workability kept and safely perform radiography.

Further, since the supporting platforms 103 and 104 and the subject platform 110 gradually have smaller sizes as their positions are closer to the radiation source 106, in the case where the supporting platforms 103 and 104 are rotated toward the side of the radiation source 106, it is possible to easily pass the subject platform 110 and the supporting platform 103 through the cut portions 103C and 104C.

Further, since the radiation image information detecting member supported by the supporting platform 103, which is the closest platform to the radiation source 106, has a larger size than the subject 8, it is possible to surely detect radiation transmitted through the subject 8 with the radiation image information detecting member. In other words, a radiation image of the subject 8 can surely be radiographed.

Here, in the second embodiment as mentioned above, the radiation image radiographing apparatus 101 is explained as an apparatus for radiographing only a phase contrast image. However, preferably, by having a structure capable of placing the radiation image information detecting member just above or below the subject platform 110, it is also possible to radiograph an absorption contrast image, which is normal radiography. In this case, when radiography is performed in the absorption contrast image radiography mode, it is possible to evacuate both the supporting platforms 103 and 104 from the space below the subject platform 110. Here, an interval between the radiation image information detecting member to be used for the absorption contrast image radiography and the radiation tube focal point 107 is preferably within the range from 60 cm to 70 cm.

Further, as mentioned above, the supporting platforms 103 and 104 support cassettes incorporating the photostimulable phosphor plate therein as the radiation image information detecting member. However, the radiation image information detecting member supported by the supporting platforms 103 and 104 is not limited to the one with the photostimulable phosphor sheet as mentioned above. For example, a radiation image information detecting member made of screen film system which is a combination of X-ray fluorescent intensifying screen and silver halide photographic film, a radiation image information detecting member where scintillators for converting radiation energy into light and light semiconductor devices for detecting the light are arrayed two-dimensionally, a radiation image information detecting member where scintillators for directly converting radiation energy into electric signals and semiconductor devices for detecting the electric signals are arrayed two-dimensionally, a radiation image information detecting member where combinations of scintillators for converting radiation into light and lenses for light-focusing the light to CCD, CMOS or the like are arrayed two-dimensionally, a radiation image information detecting member where scintillators convert radiation into light and the light is transmitted to CCD or CMOS through optical fiber for replacing it with electrical signals may be used and supported by the supporting platforms 103 and 104.

The entire disclosure of Japanese Patent Application Nos. Tokugan 2002-343117 filed on Nov. 26, 2002, Tokugan 2002-377723 filed on Dec. 26, and Tokugan 2003-313620 filed on Sep. 5, including specifications, claims, drawings and summaries are incorporated herein by reference in their entirety.

What is claimed is:

1. A radiation image radiographing apparatus for mammography which radiographs a patient in an upright position comprising:
    a radiation source;
    a subject platform for supporting a subject so as to face the subject to the radiation source while the patient is in the upright position;
    a pressure plate, which is movable up and down with respect to the subject platform, for pressing and fixing the subject; and
    a plurality of supporting platforms for supporting a radiation image information detecting member for detecting radiation image information based on radiation transmitted through the subject, said plurality of supporting platforms being positioned on an opposite side of the subject platform with respect to the radiation source;
    wherein the plurality of supporting platforms are provided at fixed distances from the radiation source, and at least two said supporting platforms are provided at respective different distances from the radiation source;
    wherein at least one of the supporting platforms is provided at a position suitable for radiographing an absorption contrast image, and at least another one of the supporting platforms is provided at a position suitable for radiographing a phase contrast image; and
    wherein each of the plurality of supporting platforms is individually movable to be evacuated from a position in which the supporting platform faces the radiation source.

2. The apparatus of claim 1, further comprising a controller including a switcher for switching between radiography modes corresponding respectively to the plurality of supporting platforms,
    wherein the controller controls irradiation conditions of the radiation source in accordance with an output of the switcher.

3. The apparatus of claim 2, wherein each of the plurality of supporting platforms comprises a sensor for detecting whether the supporting platform comprising the sensor is usable for radiography, and
    wherein at least when the phase contrast radiography is to be performed, the controller automatically obtains one of the radiography modes as a mode to be used based on an output of each sensor with respect to a status of each of the plurality of supporting platforms.

4. The apparatus of claim 2, wherein when a magnified image is radiographed using the phase contrast image radiography, the controller reduces a size of the magnified image back to substantially full scale to be output.

5. The apparatus of claim 1, wherein the radiation image information detecting member comprises a photostimulable phosphor plate.

6. The apparatus of claim 1, wherein the radiation image information detecting member comprises a flat panel detector.

7. The apparatus of claim 1, further comprising an input device for inputting a radiography mode.

8. The apparatus of claim 7, wherein the input device comprises a radiation operation panel comprising keys for selecting the radiography mode.

9. The apparatus of claim 1, wherein at least one of the plurality of supporting platforms detachably supports the radiation image information detecting member.

10. The apparatus of claim 1, wherein at least one of the plurality of supporting platforms is detachably attached to a body of the radiation image radiographing apparatus.

11. The apparatus of claim 1, wherein at least one of the plurality of supporting platforms is swingably mounted on a body of the apparatus.

12. The apparatus of claim 11, wherein the at least one of the plurality of supporting platforms comprises a cut portion, and is rotatable such that when the at least one of the plurality of supporting platforms rotates, at least a part of one of the other plurality of supporting platforms and the subject platform passes through the cut portion.

13. The apparatus of claim 11, wherein said at least one supporting platform that is provided at a position suitable for radiographing a phase contrast image comprises at least two of the plurality of supporting platforms.

14. The apparatus of claim 11, wherein sizes of the plurality of supporting platforms and the subject platform decrease as distances thereof from the radiation source become shorter.

15. The apparatus of claim 11, wherein the radiation image information detecting member supported by a supporting platform located closest to the radiation source among the plurality of supporting platforms is larger than the subject.

16. The apparatus of claim 1, wherein at least one of the plurality of supporting platforms is retractable.

17. The apparatus of claim 1, wherein at least one of the plurality of supporting platforms is mounted on a body of the apparatus to be movable along an irradiation direction of the radiation from the radiation source.

18. A radiation image radiographing apparatus comprising:
a radiation source;
a subject platform for supporting a subject so as to face the subject to the radiation source; and
a plurality of supporting platforms for supporting a radiation image information detecting member for detecting radiation image information based on radiation transmitted through the subject, said plurality of supporting platforms being positioned on an opposite side of the subject platform with respect to the radiation source;
wherein the plurality of supporting platforms are provided at fixed distances from the radiation source, and at least two said supporting platforms are provided at respective different distances from the radiation source;
wherein at least one of the supporting platforms is provided at a position suitable for radiographing an absorption contrast image, and at least another one of the supporting platforms is provided at a position suitable for radiographing a phase contrast image;
wherein each of the plurality of supporting platforms is individually movable to be evacuated from a position in which the supporting platform faces the radiation source;
wherein at least one of the plurality of supporting platforms is swingably mounted on a body of the apparatus; and
wherein the at least one of the plurality of supporting platforms comprises a cut portion, and is rotatable such that when the at least one of the plurality of supporting platforms rotates, at least a part of one of the other plurality of supporting platforms and the subject platform passes through the cut portion.

19. A radiation image radiographing apparatus comprising:
a radiation source;
a subject platform for supporting a subject so as to face the subject to the radiation source; and
a plurality of supporting platforms for supporting a radiation image information detecting member for detecting radiation image information based on radiation transmitted through the subject, said plurality of supporting platforms being positioned on an opposite side of the subject platform with respect to the radiation source;
wherein the plurality of supporting platforms are provided at fixed distances from the radiation source, and at least two said supporting platforms are provided at respective different distances from the radiation source;
wherein at least one of the supporting platforms is provided at a position suitable for radiographing an absorption contrast image, and at least another one of the supporting platforms is provided at a position suitable for radiographing a phase contrast image;
wherein each of the plurality of supporting platforms is individually movable to be evacuated from a position in which the supporting platform faces the radiation source;
wherein at least one of the plurality of supporting platforms is swingably mounted on a body of the apparatus; and
wherein sizes of the plurality of supporting platforms and the subject platform decrease as distances thereof from the radiation source become shorter.

* * * * *